United States Patent [19]

Tobkes et al.

[11] Patent Number: 5,182,374
[45] Date of Patent: Jan. 26, 1993

[54] CLINDAMYCIN PHOSPHATE SYNTHESIS

[75] Inventors: Martin Tobkes, Spring Valley; Simon Diaz; Lalitha Krishnan, both of Suffern, all of N.Y.

[73] Assignee: American Cyanamid Company, Stamford, Conn.

[21] Appl. No.: 497,039

[22] Filed: Mar. 21, 1990

[51] Int. Cl.$^5$ ............................................ C07M 11/04
[52] U.S. Cl. .................................. 536/16.5; 536/16.2
[58] Field of Search ................ 536/16.2, 16.5, 12–18.5

[56] References Cited

U.S. PATENT DOCUMENTS

| 3,487,068 | 12/1969 | Morozowich et al. | 536/16.5 |
| 4,686,208 | 8/1987 | Lockhoft et al. | 514/42 |
| 4,849,515 | 7/1989 | Matier et al. | 536/16.5 |

Primary Examiner—Johnnie R. Brown
Assistant Examiner—Elli Peselev
Attorney, Agent, or Firm—Kenneth J. Dow

[57] ABSTRACT

An improved process for producing the antibiotic compound clindamycin phosphate through the use of novel intermediate, 7(S)-chloro-7-deoxylincomycin-2-bis(2,2,2-trichloroethyl)phosphochloridate and similar compounds.

4 Claims, No Drawings

CLINDAMYCIN PHOSPHATE SYNTHESIS

FIELD OF THE INVENTION

This invention relates to an improvement in the process of producing clindamycin phosphate, an antibiotic, from clindamycin.

DESCRIPTION OF THE PRIOR ART

Clindamycin is the 7-deoxy-7-chloro derivative of lincomycin. Lincomycin, which is an antibiotic elaborated by an actinomycete, is a derivative of the amino acid trans-L-4-n-propylhygrinic acid, attached to a sulfur-containing derivative of an octose.

Both clindamycin and lincomycin are potent antibiotics which exert their effect by binding to the 50S subunit of bacterial ribosomes thereby suppressing protein synthesis. Clindamycin has an antibacterial spectrum very much like lincomycin, however it may be more potent against staphylococci and several streptococci. Clindamycin is primarily indicated for the treatment of serious intra-abdominal anaerobic infections such as those caused by bacteroides fragiles and serious respiratory infections caused by streptococci, staphylococci and pneumococci.

Clindamycin, as clindamycin hydrochloride, is well absorbed after oral administration. The presence of food in the stomach and intestine does not appear to interfere with absorption. The plasma half-life is 1.5 to 5 hours and most of the clindamycin is destroyed in the body, only about 10% being excreted in the urine. Clindamycin palmitate hydrochloride, which is converted to clindamycin in the small intestine, lacks the bitter taste of clindamycin and is thus suited to use in an oral solution for pediatric use.

The phosphate ester of clindamycin, clindamycin phosphate, is rapidly hydrolyzed in the plasma to clindamycin. It has the same actions and uses as clindamycin hydrochloride, except that the phosphate is given parenterally which avoids the gastrointestinal side effects of oral forms of clindamycin. When administered intravenously, peak serum levels of clindamycin are reached by the end of short term infusion. Biologically inactive clindamycin phosphate disappears rapidly from the serum, but the serum disappearance half-life of active clindamycin in adults is about 3 hours. After intramuscular injection, peak serum levels are reached in about 3 hours in adults. A recent study, K. I. Plaisance, G. L. Drusano, A. Forrest, R. Townsend and H. C. Standiford, Antimicrobial Agents and chemotherapy, 33, 618–620 (1989) demonstrates the rapid conversion of clindamycin phosphate to clindamycin in six normal human volunteers, with little renal elimination of the phosphate. This data suggests nearly complete bioavailability of clindamycin from the phosphate ester. Clindamycin phosphate is also available in a topical solution and topical gel for use in the treatment of acne.

Clindamycin phosphate, which has the following structure:

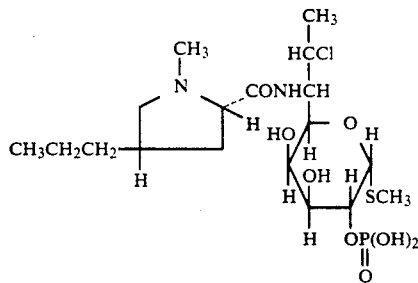

has been prepared from clindamycin hydrochloride heretofore by following the method described in U.S. Pat. No. 3,487,068 issued Dec. 30, 1969 to Morozowich et al. According to this method, the 3 and 4 hydroxyl groups are protected by condensation with an aromatic aldehyde such as cinnamaldehyde to form a 3,4-arylidene clindamycin and the 2-hydroxyl group is then condensed with phosphoryl chloride. Appropriate hydrolytic procedures finally convert the —OPOCl$_2$ residue to —OPO(OH)$_2$ and remove the protecting group. This procedure, however, has the disadvantages of requiring the use of phosphoryl chloride, a corrosive, moisture sensitive reagent. Also, the process leads to a preponderance of by-products and low yields (about 30%) and requires a cumbersome work-up.

Martier et al., in U.S. Pat. No. 4,849,515 issued July 18, 1989 discloses a process of producing clindamycin phosphate by first protecting the 3 and 4 hydroxyl groups With 2,2 dimethoxypropane followed by formation of the intermediate clindamycin 2-phosphoryl benzylate by reacting the protected clindamycin with phosphorus oxychloride and benzyl alcohol. Removal of the benzylate group by reaction with hydrogen gas in the presence of a palladium catalyst Yields clindamycin phosphate.

The present invention provides an improved method of preparing clindamycin phosphate by reaction of the protected clindamycin with a phosphochloridate compound to form novel clindamycin triester phosphate intermediates.

SUMMARY OF THE INVENTION

Accordingly, the present invention provides an improved method of producing clindamycin phosphate from clindamycin hydrochloride. The improved method produces the phosphate ester in high yield through a very efficient reaction sequence. This is accomplished through the formation of novel clindamycin-2-phosphochloridate intermediates.

In accordance with one embodiment of the present invention, clindamycin phosphate is prepared by first protecting the 3 and 4 hydroxyl groups with an appropriate blocking group such as isopropylidene. Reaction of the protected clindamycin with bis(2,2,2-trichloroethyl) phosphochloridate or a similar compound in the presence of iodide ion yields the novel crystalline clindamycin-2-phosphoohloridate intermediate. Treatment with zinc in a suitable solvent then yields the blocked dihydrogen phosphate. Removal of the blocking group results in the desired product, clindamycin phosphate.

DETAILED DESCRIPTION

The novel process of the present invention may be described by the following reaction scheme:

Scheme

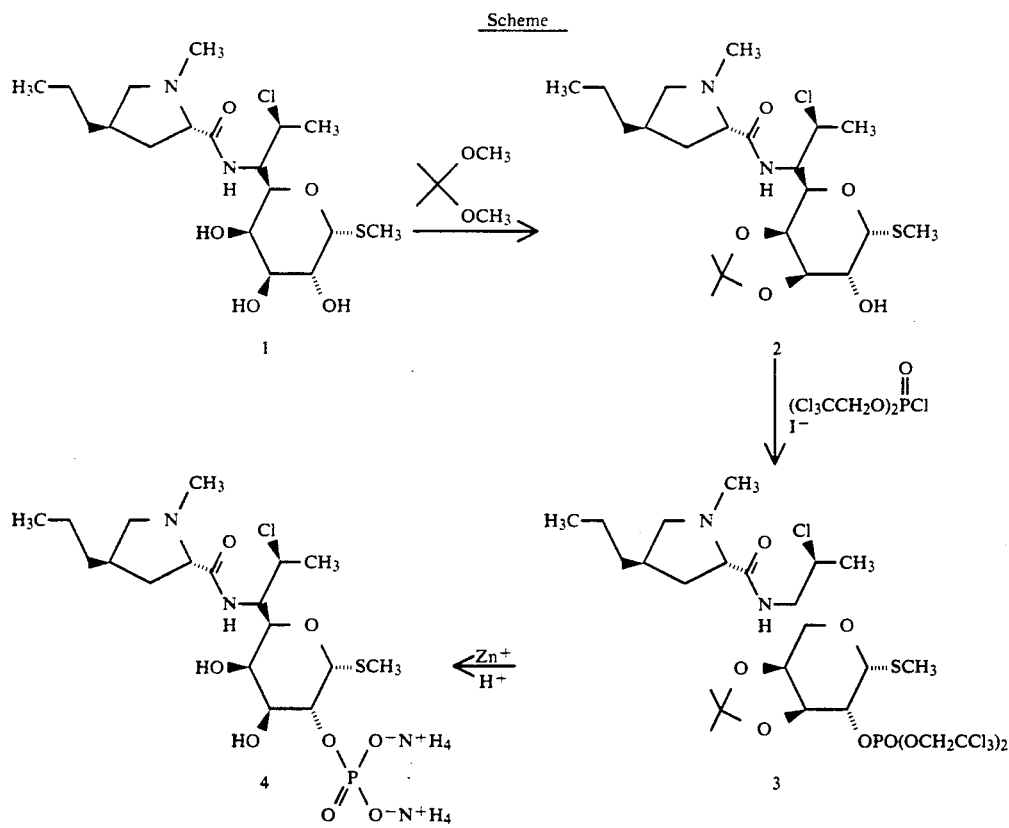

Clindamycin hydrochloride may be prepared in accordance with the description in U.S. Pat. No. 3,487,068 issued Dec. 30, 1969.

In one embodiment of the present invention and in accordance with the preceding reaction scheme, the clindamycin hydrochloride 1 is first condensed with an appropriate blocking reagent, such as 2,2-dimethoxypropane to yield the protected clindamycin 2. Reaction of 2 with bis-(2,2,2-trichloroethyl)phosphochloridate in the presence of iodide ion occurs in high yield to give the crystalline phosphate ester 3, Which may be further purified by recrystallization. Treatment of 3 with zinc in acetic acid-pyridine affords the blocked dihydrogen phosphate. Deblocking to form the desired product is effected by heating with a mixture of dilute aqueous sulfuric acid and acetic acid. The compound is purified by passing a solution thereof through a strong acid cation exchange column followed by elution with dilute aqueous ammonia. The ammonium salt 4 thus obtained may be converted to the free acid by common procedures known to those skilled in the art.

The advantage of the foregoing procedure lies in the substitution of the bis(2,2,2-trichloroethyl)-phosphorochloridate for phosphoryl chloride as the phosphorylating agent. This avoids many of the disadvantages associated with the use of phosphoryl chloride, which is a corrosive, moisture sensitive reagent. Further, the use of the present phosphorochloridate phosphorylating agent provides for a clean reaction with less by-products and a reaction scheme which produces the desired compound in high yields. The synthetic procedure described herein affords a ninety (90) percent yield without any optimization work performed on it. A product of high purity is obtained because the bis-2,2,2-trichloro-ethyl triester phosphate can be crystallized out from the reaction mixture.

In the foregoing reaction scheme, the blocking group may be isopropylidine or alkylidenes. Accordingly, the protected clindamycin compound may be formed by reaction of clindamycin with any carbonyl compound of the following formula:

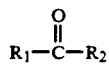

where $R_1$ is lower alkyl and $R_2$ is lower alkyl or hydrogen. Preferably, the blocking group is an alkylidene compound such as that derived from 2,2-dimethoxypropane, a common solvent derived from acetone.

Likewise, the phosphorylating agent is not limited to (2,2,2-trichloroethyl) phosphorochloridate but may also be any of the compounds of the following formulae:

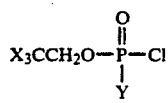

wherein X is Cl or Br and Y is

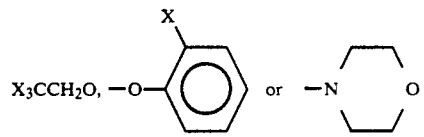

As shown in the foregoing reaction scheme, the tertiary phosphate esters 3 may be converted to the desired primary ester by treatment with zinc. A subsequent treatment with base or mono(trialkylammonium) phosphate may be necessary.

Removal of the blocking group from the 3, 4 hydroxy positions may be effected by heating with dilute acid such as acetic acid or mineral acid. The former is preferable for arylidene blocking groups and the latter for alkylidene groups. The reaction mixture may be purified by passing through a suitable strong acid cationic exchange resin or a suitable quarternary ion exchange resin.

The invention will be described in greater detail in conjunction with the following non-limiting examples.

EXAMPLE 1

Preparation of Protected Clindamycin:

Methyl[2S-(2α,4β)]-7-chloro-6,7-dideoxy-3,4-O-(1-methylethylidene)-6-[[(1-methyl-4-propyl-2-pyrrolidinyl)carbonyl]amino]-1-thio-L-threo-α-D-galactooctopyranoside (clindamycin acetonide)

A solution of 850 mg of clindamycin free base, in a solvent mixture of 20 ml of 2,2-dimethoxypropane and 5 ml of acetone containing 520 mg of p-toluenesulfonic acid is stirred at ambient temperature for 3 hours. The mixture is evaporated to dryness in vacuo and the residue partitioned between 5% sodium o bicarbonate and ethyl acetate. The extract is dried ($Na_2SO_4$), filtered and hexane added to the boiling solvent to give 750 mg of the desired product as a solid. (m.p. 162°-163° C.)

EXAMPLE 2

Preparation of Protected Clindamycin 2-phosphoro Chloridate Intermediate:

Methyl[2S-(2α,4β)]-7-chloro-6,7-dideoxy-3,4-O-(1-meth ylethylidene)-6-[[(1-methyl-4-propyl-2-pyrrolidinyl) cerbonyl]amino]-1-thio-L-threo-α-D-galactooctopyrano side 2-[bis(2,2,2-trichlorethylphosphate]

A solution of 93o mg of clindamycin acetonide and 330 mg of sodium iodide in s ml of pyridine is stirred at ambient temperature while 1.8 g of bis(2,2,2-trichloroethyl) phosphorochloridate is added followed by continued stirring for 3 hours. The pyridine is evaporated in vacuo to a residue which is dissolved in dichloromethane and Washed With a 20% $Na_2S_2O_4$ solution. The organic layer is dried ($Na_2SO_4$) and evaporated to give a gum which is dissolved in 50 ml of dichloromethane and stirred with 3 g of activated magnesium silicate, filtered, then evaporated. The residue is crystallized from ethyl acetate:hexane to give 1.4 g of the desired product. (mp 132°-134° C.)

EXAMPLE 3

Preparation of Clindamycin Phosphate

Methyl-7-chloro-6,7,8-trideoxy-6-(1-methyltrans -4-propyl-L-2-pyrrolidinecarboxamide)-1-thio-L-threo-α-D-galacto -octopyranoside phosphate (clindamycin phosphate)

A solution of 808 mg of the phosphorylated ester in 6 ml of pyridine and 16 ml of acetic acid is stirred at ambient temperature while s5 mg of zinc is rapidly added. The mixture is filtered after one hour and evaporated to a residue which is heated with stirring at 50° C. for 2 hours with a solvent mixture of 2 ml of acetic acid, and 4 ml of 0.5N sulfuric acid. The mixture is cooled and filtered followed by evaporation of the filtrate in vacuo to a residue, which is chromatographed on a suitable ion-exchange resin, in the acid form, and eluted with 2% ammonium hydroxide. The desired product is obtained as ammonium salt by evaporation of the product fractions. (dec. 212° C.)

We claim:

1. A compound of the formula:

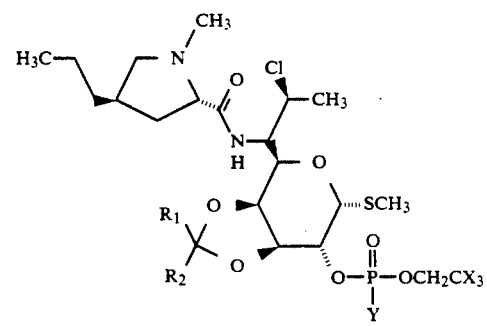

where $R_1$ is lower alkyl, $R_2$ is lower alkyl or hydrogen, X is Cl or Br and Y is

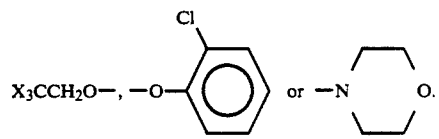

2. A compound of the formula:

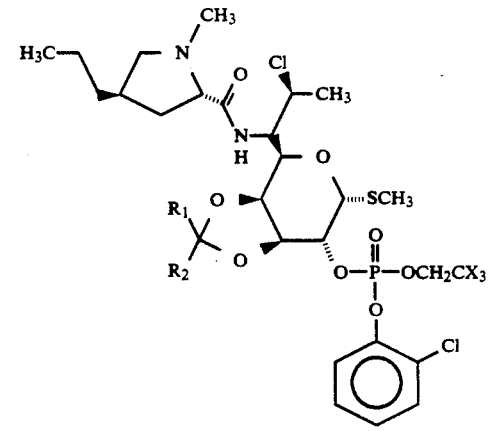

wherein X is Cl or Br, $R_1$ is lower alkyl, and $R_2$ is lower alkyl or hydrogen.

3. A compound of the formula:

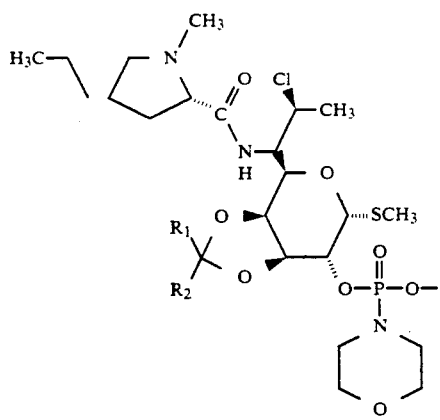
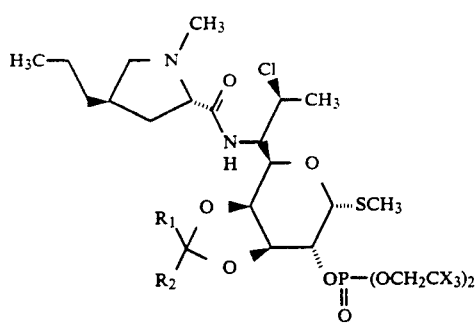
wherein X is Cl or Br, $R_1$ is lower alkyl and $R_2$ is lower alkyl or hydrogen.
4. A compound of the formula:
where $R_1$ is lower alkyl, $R_2$ is lower alkyl or hydrogen and X is Cl or Br.
* * * * *